(12) United States Patent
Buri et al.

(10) Patent No.: US 9,017,518 B2
(45) Date of Patent: Apr. 28, 2015

(54) PROCESS FOR THE PREPARATION OF SURFACE-TREATED CALCIUM CARBONATE MATERIAL AND USE OF SAME IN THE CONTROL OF ORGANIC MATERIAL IN AN AQUEOUS MEDIUM

(71) Applicants: Matthias Buri, Rothrist (CH); Samuel Rentsch, Aarburg (CH); Patrick A. C. Gane, Rothrist (CH); Daniel Gantenbein, Elnesvagen (NO); Joachim Schölkopf, Killwangen (CH)

(72) Inventors: Matthias Buri, Rothrist (CH); Samuel Rentsch, Aarburg (CH); Patrick A. C. Gane, Rothrist (CH); Daniel Gantenbein, Elnesvagen (NO); Joachim Schölkopf, Killwangen (CH)

(73) Assignee: Omya International AG, Oftringen (CH)

( * ) Notice: Subject to any disclaimer, the term of this patent is extended or adjusted under 35 U.S.C. 154(b) by 0 days.

(21) Appl. No.: 14/284,567

(22) Filed: May 22, 2014

(65) Prior Publication Data
US 2014/0251564 A1 Sep. 11, 2014

Related U.S. Application Data

(62) Division of application No. 13/807,940, filed as application No. PCT/EP2011/061869 on Jul. 12, 2011.

(60) Provisional application No. 61/500,171, filed on Jun. 23, 2011.

(30) Foreign Application Priority Data

Jul. 20, 2010 (EP) .................................... 10170110

(51) Int. Cl.
| | |
|---|---|
| *D21F 11/00* | (2006.01) |
| *C02F 1/68* | (2006.01) |
| *C09C 1/02* | (2006.01) |
| *B01J 20/22* | (2006.01) |
| *C02F 1/28* | (2006.01) |
| *C07C 68/04* | (2006.01) |
| *D21H 17/14* | (2006.01) |

(52) U.S. Cl.
CPC ........... *C02F 1/682* (2013.01); *Y10T 428/2982* (2015.01); *C01P 2004/51* (2013.01); *C01P 2004/62* (2013.01); *C01P 2006/12* (2013.01); *C02F 1/681* (2013.01); *C09C 1/021* (2013.01); *B01J 20/223* (2013.01); *C02F 1/288* (2013.01); *C07C 68/04* (2013.01); *D21H 17/14* (2013.01); *C02F 1/281* (2013.01)

(58) Field of Classification Search
USPC ......................................................... 162/141
See application file for complete search history.

(56) References Cited

U.S. PATENT DOCUMENTS

| | | | |
|---|---|---|---|
| 2,462,204 | A | 3/1949 | Baker |
| 3,382,170 | A | 5/1968 | Pape |
| 3,414,511 | A | 12/1968 | Hitzman |
| 3,696,051 | A | 10/1972 | McGuire et al. |
| 3,855,152 | A | 12/1974 | Preus |
| 4,011,175 | A | 3/1977 | Preus |
| 4,786,432 | A | 11/1988 | Kanfer et al. |
| 5,035,804 | A | 7/1991 | Stowe |
| 7,977,410 | B2 | 7/2011 | Nagamatsu et al. |
| 2002/0102404 | A1 | 8/2002 | Nakai et al. |
| 2008/0182933 | A1 | 7/2008 | Shimizu et al. |
| 2012/0283368 | A1 | 11/2012 | Nagamatsu et al. |

FOREIGN PATENT DOCUMENTS

| | | |
|---|---|---|
| EP | 1980588 A1 | 10/2008 |
| EP | 2159258 A1 | 3/2010 |
| JP | 2005336417 A | 12/2005 |
| WO | WO0039222 A1 | 7/2000 |
| WO | 2004083316 A1 | 9/2004 |
| WO | 2005012157 A2 | 12/2005 |
| WO | 2008077877 A2 | 7/2008 |
| WO | 2008113839 A1 | 9/2008 |
| WO | 2008125955 A1 | 10/2008 |
| WO | 2009074492 A1 | 6/2009 |
| WO | 2010023144 A1 | 3/2010 |

OTHER PUBLICATIONS

International Search Report dated Oct. 7, 2011 for PCT Application No. PCT/EP2011/061869.
Written Opinion of the International Searching Authority dated Oct. 7, 2011 for PCT Application No. PCT/EP2011/061869.
Office Action dated Jan. 24, 2014 for Chinese Application No. 201180035279.1.
Office Action dated Sep. 2, 2014 for Japanese Patent Application No. JP 2013520062.

*Primary Examiner* — Mark Halpern
(74) *Attorney, Agent, or Firm* — Amster, Rothstein & Ebenstein LLP

(57) ABSTRACT

The present invention relates to a process for the production of a surface-treated calcium carbonate, the use of this surface-treated calcium carbonate in a process for the control of organic material in an aqueous medium, as well as to a composite of surface-treated calcium carbonate and organic material, such as a composite of surface-treated calcium carbonate and to the use of such a composite.

31 Claims, No Drawings

PROCESS FOR THE PREPARATION OF SURFACE-TREATED CALCIUM CARBONATE MATERIAL AND USE OF SAME IN THE CONTROL OF ORGANIC MATERIAL IN AN AQUEOUS MEDIUM

CROSS-REFERENCE TO RELATED APPLICATION

This is a divisional of U.S. application Ser. No. 13/807,940, filed Feb. 6, 2013, which is a U.S. national phase of PCT Application No. PCT/EP2011/061869, filed Jul. 12, 2011, which claims priority to European Application No. 10170110.0, filed Jul. 20, 2010 and U.S. Provisional Application No. 61/500,171, filed Jun. 23, 2011, the contents of which are hereby incorporated by reference.

The present invention relates to a process for the preparation of surface-treated calcium carbonate material, the surface-treated calcium carbonate material obtained thereby, the use of this surface-treated calcium carbonate material for the control of organic material, as well as to a composite of surface-treated calcium carbonate and organic material and its uses.

Organic material characterised as "sticky", i.e. presenting a relatively high degree of tackiness and/or adhesiveness relative to certain surfaces, presents problems in a variety of contexts. Oily organic material, such as petroleum and its derivatives, released in natural aqueous mediums have been associated with environmental catastrophes when such substances adhere to the internal or external surfaces of species (e.g. to bird wings or lung surfaces) in contact with this environment.

A number of treatments to remove oil from the surface of water have been developed. Sawdust, peat fibers, diatomaceous earth, expanded perlite and vermiculite have all been used to soak up oil, as mentioned in U.S. Pat. No. 3,414,511. In view of the same aim, U.S. Pat. No. 3,855,152 and U.S. Pat. No. 4,011,175 refer to the use of expanded perlite mixed with asphalt, cellulose fibers and clay to form a mixture to be spread on oil spills.

The prior art also refers to surface-treated materials for this purpose, as in U.S. Pat. No. 3,382,170, wherein expanded perlite coated with silicone is employed. In JP 74 45,467, perlite granules are coated with polypropylene to produce oleophilic-hydrophobic granules for the treatment of oil spills, while U.S. Pat. No. 3,696,051 refers to the use of vermiculite coated with a metallic cyclopentadienyl compound. In U.S. Pat. No. 2,464,204, a mineral aggregate such as sand is mixed with petroleum asphalt and fuel oil and heated to form aggregated particles having a coating of solid carbon. U.S. Pat. No. 5,035,804 refers to compositions comprising a fine grained particulate material, such as expanded perlite or vermiculite, or sand, coated with an oleophilic/hydrophobic layer comprising sulfur, a metallic sulphate, an alkali metal nitrate, and burned hydrocarbon oil.

Sticky organic materials, including for example silicone rubbers and defoamers, also present a problem in the paper industry, where "pitch problems" or "stickies problems" are known to occur, reported mainly as a deposition of organic sticky material coming out of water suspension either onto the papermaking equipment or as spots in the paper web itself.

The primary fibre source in papermaking is wood, which is reduced to its constituent fibres during pulping by combinations of grinding, thermal and chemical treatment. During this process the natural resin contained within the wood is released into the process water in the form of microscopic droplets. These droplets are referred to as pitch. Problems arise when colloidal pitch becomes destabilised from the original emulsion form and is deposited on the surfaces in the wet-end circuit of a paper mill, where the particles can form agglomerates, which eventually break loose and appear as visible spots in the paper, ranging from yellow to black in colour.

Today, increasingly, papermaking pH is either neutral or slightly alkaline, such that the removal of pitch is no longer an automatic corollary of the use of alum. The increase in pH to pseudo-neutral is a growing trend in mechanical papers and so the study of pitch removal under these conditions is also of growing importance. Moreover, mechanical pulps carry over much more dissolved and colloidal matter than chemical pulps and recycled pulps.

For completeness, the Applicant would like to mention the following patent applications in its name referring to pitch control. WO 2008/077877 mentions a wet-ground bentonite and talc that is useful to target white pitch. WO 2008/113839 refers to a process for the control of pitch in an aqueous medium, wherein surface-reacted natural calcium carbonate or an aqueous suspension comprising surface-reacted calcium carbonate and having a pH of greater than 6.0 measured at 20° C., is added to the medium, wherein the surface-reacted calcium carbonate is a reaction product of natural calcium carbonate with carbon dioxide and one or more acids.

Furthermore, the Applicant would like to mention the following patent applications in its name referring to surface-treated calcium carbonate for use in plastic applications. WO 2005/121257 refers to a dry mineral pigment characterised in that it contains a product formed in situ by the multiple reaction between a calcium carbonate and one or more moderately strong to strong $H_3O^+$ ion donators, gaseous $CO_2$ and one or more compounds of formula R—X, where R—X represents a carbonaceous radical and X represents groups such as carboxylic, amine, hydroxyl, phosphonic, or their mixtures. WO 2008/125955 mentions a process for the preparation of a treated mineral filler product having reduced volatiles, where the process comprises the steps of treating at least one dry mineral filler with at least one Group II or Group III salt of a $C_8$ to $C_{24}$ aliphatic monocarboxylic acid to produce an intermediate mineral filler product, followed by treating the intermediate mineral filler product with at least one $C_8$ to $C_{24}$ aliphatic monocarboxylic acid to produce a treated mineral filler product. Finally, WO 2010/023144 refers to a treated mineral filler product comprising: at least one mineral filler and a treatment layer located on the surface of said mineral filler(s), where said treatment layer comprises at least one saturated $C_8$ to $C_{24}$ aliphatic carboxylic acid; and at least one di and/or trivalent cation salt of one or more saturated $C_8$ to $C_{24}$ aliphatic carboxylic acid, where the weight ratio of all of said aliphatic carboxylic acid salt(s):all of said aliphatic carboxylic acid(s) is from 51:49 to 75:25; and said treatment layer is present in an amount of at least 2.5 mg/m$^2$ of said mineral filler.

Lastly, the Applicant would mention unpublished European patent applications 09167246.9 and 10151846.2, which mention the use of AMP and PEI, respectively, as additives in a mineral suspension used in order to increase the suspension pH while limiting conductivity changes. Unpublished European patent application 09178228.4 mentions the use of monoalcohol primary alkanolamines as biocide enhancers, while unpublished European patent application 10157099.2 mentions modified polyalkyleneimines as flotation aid.

Talc is accepted as an effective control agent for pitch deposits and has been used in the treatment of oil spills. It is assumed that talc reduces tackiness of organic substances such as pitch and petroleum, by covering the surfaces of their oily agglomerates.

However, as it is necessary to target not only organic material residing at the surface of an aqueous medium, but also colloidal organic material that is dispersed within this environment, it is desirable to provide a treatment agent in the form of an aqueous suspension. Treatment agents such as talc present the drawback that they must be extensively surface-treated and/or mechanically sheared in order to become sufficiently wetted to enter the bulk of the aqueous phase.

Therefore, there is a continuous need for alternative economic materials that are readily available, which may be provided in the form of an aqueous suspension and which are capable of controlling organic material both within and on the surface of aqueous systems.

The above objective has surprisingly been solved by the inventive process for the preparation of calcium carbonate material surface-treated with one or more salts of a $C_5$-$C_{28}$ fatty acid, the surface-treated calcium carbonate material obtained thereby, and the addition of this surface-treated calcium carbonate material or an aqueous suspension comprising this surface-treated calcium carbonate material to an aqueous medium, in order to control the organic material contained in the aqueous medium.

The product obtained by the control process, that is to say a composite material formed of surface-treated calcium carbonate material and organic material, is also an object of the present invention. Such composite materials may find a variety of applications, including as a filler in paper.

For the purpose of the present invention, "control" of an organic material in an aqueous medium shall mean (1) the reduction of the tackiness of this organic material, and/or (2) the association of this organic material to form a composite, and/or (3) the reduction of the aqueous phase chemical oxygen demand (COD). The latter may be measured as in the Example section below. The formation of a composite is evaluated by a decrease in turbidity of the aqueous medium, and may be measured as described in the Examples section below.

The process for the preparation of surface-treated calcium carbonate material according to the present invention comprises the following steps:
a) providing at least one calcium carbonate-containing material;
b) providing at least one salt of a $C_5$-$C_{28}$ fatty acid selected from the group comprising mono-alcohol primary alkanolamine salts, polyethyleneimine salts, and mixtures thereof;
c) treating said calcium carbonate-containing material of step a) by contacting it with said fatty acid salt(s) of step b);
d) obtaining a surface-treated calcium carbonate material.

Preferably, the calcium carbonate of said calcium-carbonate containing material is selected from the group comprising ground natural calcium carbonate, dolomite, precipitated calcium carbonate and mixtures thereof. Said calcium carbonate may be present in said calcium-carbonate containing material in combination with further minerals, such as talc and/or mica.

Dolomite refers to dolomite mineral and is calcium magnesium carbonate, i.e. $CaMg(CO_3)_2$. Dolomite mineral is found either in dolomite rock, consisting essentially entirely of dolomite, or in association with calcium carbonate in dolomitic limestone.

"Ground natural calcium carbonate" (GNCC) in the meaning of the present invention is a calcium carbonate obtained from natural sources, such as limestone, marble or chalk, and processed through a treatment such as grinding, screening and/or fractionising by wet and/or dry, for example by a cyclone, classifier or centrifuge.

"Precipitated calcium carbonate" (PCC) in the meaning of the present invention is a synthesized material, generally obtained by precipitation following reaction of carbon dioxide and lime in an aqueous medium or by precipitation of a calcium and carbonate ion source in water. PCC may be metastable vaterite, stable calcite or aragonite. In one embodiment, this PCC may be ground.

Said GNCC or PCC may be surface reacted to form a surface-reacted calcium carbonate, which are materials comprising GNCC and/or PCC and an insoluble, at least partially crystalline, non-carbonate calcium salt extending from the surface of at least part of the calcium carbonate. Such surface-reacted products may, for example, be prepared according to WO 00/39222, WO 2004/083316, WO 2005/121257, WO 2009/074492, unpublished European patent application with filing number 09162727.3, and unpublished European patent application with filing number 09162738.0.

Said calcium-carbonate containing material of step a) preferably contains at least 50%, preferably at least 90% by weight of calcium carbonate relative to the total weight of said calcium-carbonate containing material.

In a preferred embodiment, 10 to 90%, preferably 30 to 85%, more preferably 60 to 80% by weight of the calcium carbonate material particles present, prior to treatment, a particle diameter of less than 1 µm as measured according to the measurement method in the Examples section herebelow.

In another preferred embodiment, 80 to 97%, preferably 90 to 98% by weight of the calcium carbonate material particles present, prior to treatment, a particle diameter of less than 2 µm as measured according to the measurement method in the Examples section herebelow.

In another preferred embodiment, the median diameter of the calcium carbonate material particles presents, prior to treatment, a $d_{50}$ value of from 0.4 to 5 µm, preferably of from 0.5 to 1 µm, as measured according to the Example section hereafter.

In a preferred embodiment, the calcium carbonate material presents a BET specific surface area before treatment of 1 to 200 $m^2/g$, preferably of 7 to 15 $m^2/g$, as measured according to the measurement method provided in the Examples section herebelow.

In one embodiment, said calcium-carbonate containing material of step a) is provided in the form of an aqueous suspension. In this embodiment, said suspension has a content of calcium carbonate containing material within the range of 1 wt.-% to 79 wt.-%, more preferably of 3 wt.-% to 78 wt.-%, even more preferably of 55 wt.-% to 75 wt.-%, based on the weight of the suspension. Though said calcium-carbonate containing material may be dispersed with a dispersant or pre-ground with a grinding aid, such as a polyacrylate-based dispersant or grinding aid, it is preferred that said calcium-carbonate containing material in suspension be free of dispersant or grinding aid. If dispersant or grinding aid is employed, it is preferred that it is dosed in a low amount, i.e. from 0.02 to 0.5% by dry weight relative to the dry weight of calcium-carbonate containing material. In an alternative embodiment, dispersant or grinding aid is present in an amount corresponding to 0.05 to 1 $mg/m^2$ of calcium-carbonate containing material, the $m^2$ of calcium-carbonate containing material being determined based on the BET surface area measurement described in the Examples section hereafter.

According to the present invention, at least one calcium carbonate material is surface treated with one or more salts of a $C_5$-$C_{28}$ fatty acid selected from the group comprising monoalcohol primary alkanolamine salts, polyethyleneimine salts and mixtures thereof.

In a preferred embodiment, said salt of a $C_5$-$C_{28}$ fatty acid is a salt of a $C_6$-$C_{24}$ fatty acid, more preferably a salt of a $C_8$-$C_{18}$ fatty acid.

In a preferred embodiment, said salt of a $C_5$-$C_{28}$ fatty acid is a salt of a fatty acid having an iodine number of less than 5 g $I_2$/100 g of fatty acid salt. The iodine number determination is well-known to the skilled man, and namely involves iodine addition to a 100 g fatty acid sample followed by back-titration of the surplus iodine solution with sodium thiosulphate.

In a preferred embodiment, said salt of a $C_5$-$C_{28}$ fatty acid is a salt of a linear fatty acid if said fatty acid is a $C_6$-$C_9$ fatty acid.

In a most preferred embodiment, said salt of a $C_5$-$C_{28}$ fatty acid is a blend of palmitic acid salt(s) and stearic acid salt(s), preferably in a weight ratio based on the fatty acids of palmitic acid:stearic acid of 2:1 to 1:2.

Said salt of a $C_5$-$C_{28}$ fatty acid is preferably 30 to 110 mole % neutralised with said mono-alcohol primary alkanolamine and/or a polyethyleneimine. In the case of a polyethyleneimine salt, said salt of a $C_5$-$C_{28}$ fatty acid is preferably 35 to 45 mole % neutralised. In the case of a mono-alcohol primary alkanolamine, said salt of a $C_5$-$C_{28}$ fatty acid is preferably 90 to 100 mole % neutralised. The mole % neutralisation is determined based on the number of moles of fatty acid to be neutralised. A mole % neutralisation in excess of 100 mole % means that excess mono-alcohol primary alkanolamine and/or a polyethyleneimine is added during the neutralisation process.

If said salt of a $C_5$-$C_{28}$ fatty acid is a polyethyleneimine salt, it is preferred that said polyethyleneimine be linear. In this case, said polyethyleneimine preferably has a molecular weight of from 140 to 700 g/mol, and preferably of from 146 to 232 g/mol. For the purpose of the present invention, the "molecular weight" of linear polyethyleneimine is directly calculated from the respective chemical formula.

Said polyethyleneimine may also be a branched polyethyleneimine, which preferably has a molecular weight of from 500 to 50 000 g/mol, and more preferably of from 800 to 25 000 g/mol. The "molecular weight" of branched polyalkyleneimines prior to modification in the meaning of the present invention is the weight average molecular weight as measured by light scattering (LS) techniques.

If said salt of a $C_5$-$C_{28}$ fatty acid is a monoalcohol primary alkanolamine salt, said monoalcohol primary alkanolamine is preferably selected from the group comprising ethanolamine, propanolamines, butanolamines, pentanolamines and mixtures thereof.

In a most preferred embodiment, said salt of a $C_5$-$C_{28}$ fatty acid is a 1-amino-2-propanol salt of a $C_5$-$C_{28}$ fatty acid.

Said calcium carbonate-containing material(s) is preferably treated with a total of 0.1 to 3 wt. %, preferably 0.5 to 2 wt. %, based on the dry weight of said calcium carbonate-containing material(s), of said salt(s) of $C_5$-$C_{28}$ fatty acid(s).

In an alternative embodiment, said calcium carbonate-containing material(s) is treated with a total of 0.2 to 5 mg of said salt(s) of $C_5$-$C_{28}$ fatty acid(s) per $m^2$ of calcium carbonate-containing material, and preferably with 0.5 to 2 mg of said salt(s) of $C_5$-$C_{28}$ fatty acid(s) per $m^2$ of calcium carbonate-containing material, where said $m^2$ of calcium carbonate-containing material is determined based to the BET measurements made as described in the Examples section hereinbelow.

Said calcium-carbonate containing material may be treated by contacting said salt(s) of $C_5$-$C_{28}$ fatty acid(s) with said calcium carbonate-containing material in either a dry or wet, e.g. aqueous, environment.

This dry or wet treatment process may take place by mixing and/or grinding said $C_5$-$C_{28}$ fatty acid salt(s) with said calcium carbonate-containing material at a temperature of from 5 to 150° C.

Grinding may be accomplished in a grinder and may result from an autogenous grinding operation, in which the particles for grinding are subjected to mutual impacts, or may result from additional impacts with one or more other grinding media, such as grinding balls, grinding bars or grinding spindles. Such grinding with grinding media may take place, for example, in a ball-mill, such as manufactured by the company Dynomill, a vibration grinder or a wheel grinder. Depending on the type of grinding, said grinding may take place in a stationary or rotary grinding chamber. Said salt(s) of $C_5$-$C_{28}$ fatty acid(s) may be added to the calcium-carbonate containing material feed and/or into the grinding chamber, prior to and/or in the course of the grinding process.

In the case of a ball-mill, the grinding balls which are employed preferably have a Brinell hardness of between 510 and 600. Preferentially they are made of iron, such as iron-based alloys with molybdenum or chromium, porcelain and/or silicates, and they have an average ball diameter of between 0.1 and 5 mm, preferentially of between 0.2 and 3 mm, and more preferentially of between 0.5 and 5 mm. According to another preferred aspect, these grinding balls are present in a weight ratio relative to the material for grinding contained in the ball-mill of between 10:1 to 100 to 1, preferably of 20:1 to 80:1, more preferably from 30:1 to 60:1.

In the case where the treatment process is a wet treatment process, the aqueous treatment environment may be provided by providing said calcium carbonate-containing material in the form of an aqueous suspension and/or by providing said salt(s) of $C_5$-$C_{28}$ fatty acid(s) in the form of an aqueous solution or suspension.

Said salt solution or suspension preferably has a solids content of 5 to 50% by weight. It is also possible to use a dry salt; in such a case, said salt is preferably liquid at 23° C.

If the treatment process is a wet treatment process, the obtained aqueous suspension can, in one embodiment, be dried, thereby obtaining the surface-treated calcium carbonate in the form of granules or a powder.

If the treatment process is a dry treatment process, the obtained granules or powder may be introduced into an aqueous medium, thereby obtaining the surface-treated calcium carbonate in the form of an aqueous suspension.

As mentioned above the surface-treated calcium carbonate material obtained by the process of the present invention is a further object of the present invention.

Preferably, the surface-treated calcium carbonate material comprises 97 to 99% by weight of a calcium carbonate material, 0.1 to 3% by weight of monoalcohol primary monoalkanol amine and/or polyethyleneimine salt(s) of $C_5$-$C_{28}$ fatty acid(s) and 0 to 1.5% by weight of calcium and/or magnesium salt(s) of $C_5$-$C_{28}$ fatty acid(s).

Furthermore, it has surprisingly been found that the surface-treated calcium carbonate material obtained by the process according to the present invention may advantageously be used for controlling organic material in an aqueous medium.

Thus not only the use of the surface-treated calcium carbonate material obtained by the process according to the present invention for controlling organic material in an aqueous medium is an aspect, but also a process for the control of organic material in an aqueous medium, wherein said surface-treated calcium carbonate material or an aqueous suspension comprising surface-treated calcium carbonate material is added to the medium, wherein the calcium carbonate is surface treated with one or more salt(s) of a $C_5$-$C_{28}$ fatty acid, selected from the group comprising mono-alcohol primary alkanolamine salts and polyethyleneimine salts.

Said organic material(s) in an aqueous medium that may be controlled through the use of said surface-treated calcium carbonate include any lipophilic organic material(s), such as petroleum, petroleum derivatives, stickies, silicone rubbers, white pitch (such as issued from latex), pitch and mixtures thereof.

For the purpose of the present invention, organic material that may be controlled by the present invention includes pure organic materials and/or materials in which one or more inorganic materials are partially or fully covered by an organic material.

Petroleum, also referred to as crude oil, comprises a mixture of hydrocarbons of various weights, notably paraffins, naphthenes, aromatic and asphaltic(s) hydrocarbons, along with sulphur- and/or nitrogen- and/or oxygen containing organics. The exact composition of petroleum is often a function of the reservoir from which it is extracted. It may generally be extracted from oil wells or from oil or tar sands.

Petroleum derivatives include organic compounds obtained by crude oil distillation or refining, and organic compounds obtained from thermal or catalytic cracking of fractions of crude oil.

"Stickies" in the meaning of the present invention are intended to refer to sticky organic materials resulting from paper recycling. During paper recycling, hot melt glues, binders and other thermoplastic materials, for example from book-backs and adhesives tape or from silicone based defoamers may lead to the formation of so-called "stickies". These mostly exhibit varying degrees of hydrophobicity. They tend to be pliable organic materials, such as styrene-butadiene binders, latex in general which is also termed "white pitch" when causing problems in the paper machine wet end, rubber, vinyl acrylates, polyisoprene, polybutadiene, hot melts, etc. Under certain conditions, these compounds can become tacky and deposit in the paper machine. The deposits can lead to breaks in the paper or appear as visible spots, often darkened by heat, in the final product, resulting in loss of paper quality and downtime to clean the paper machine.

The chemical composition of pitch is generally divided into four classes of lipophilic components: i) fats and fatty acids, ii) steryl esters and sterols, iii) terpenoids, and iv) waxes. The chemical composition depends on the fibre source, such as variety of tree, and on the seasonal growth from which the sample is produced.

The formation of pitch can be described conceptually as developing via three main mechanisms. The first mechanistic route is the formation of an organic film of material, which can be transparent or translucent. Its thickness varies according to its concentration and the film needs a nucleus to form an initial coalescence. This type of pitch, as its formation mechanism suggests, is called filmy. The second type of pitch is one that is able to coagulate and form globules of 0.1-1.0 μm diameter, and thus is termed globular pitch. The third type of pitch commonly developed is an agglomerated, or pitch ball form and is often noticed in systems having the greatest problems with pitch deposition. The balls formed are of 1-120 μm diameter. In the filmy or globular state, the pitch does not generally cause problems, but once agglomerates have been formed then paper quality problems start to occur.

In a preferred embodiment, the pitch in said aqueous medium is non-ionic and/or anionic.

The total amount of such organic material in the aqueous medium prior to the addition of said surface-treated calcium carbonate, evaluated based on the Chemical Oxygen Demand (COD), is preferably from 1 000 to 5 000 mg $O_2$/dm$^3$, as measured according to the measurement method provided in the Examples section herebelow.

The pH, as measured in the Examples section herebelow, of the aqueous medium prior to the addition of said surface-treated calcium carbonate is preferably greater than 6, more preferably greater than 7.

In the process for the control of organic material according to the present invention, the surface-treated calcium carbonate is added to the organic material-containing aqueous medium by any conventional feeding means known to the skilled person. The surface-treated calcium carbonate can be added as an aqueous suspension, e.g. the suspension described above. Alternatively, it can be added in solid form, e.g. in the form of granules or a powder or in the form of a cake. Within the context of the present invention, it is also possible to provide an immobile phase, e.g. in the form of a cake or layer, comprising the surface-treated calcium carbonate, the aqueous medium running through said immobile phase.

Preferably, the surface-treated calcium carbonate is suspended in the organic material-containing aqueous medium, e.g. by agitation means. The amount of surface-treated calcium carbonate depends on the type of organic material to be controlled. Preferably, said surface-treated calcium carbonate is dosed in the aqueous medium in an amount corresponding to 0.05 to 5 wt.-%, more preferably 0.1 to 1 wt.-% and most preferably 0.15 to 0.5 wt.-% per 1,000 mg $O_2$/dm$^3$, wherein said mg $O_2$/dm$^3$ is determined by the COD measurement method described in the Examples section herebelow.

In one preferred embodiment of the present invention, the surface-treated calcium carbonate is added to a pitch containing aqueous media, such as mechanical pulp, e.g. ground wood, TMP (thermo mechanical pulp), or chemothermomechanical pulp (CTMP), as well as chemical pulp, e.g. kraft pulp or sulphate pulp, or recycled pulp used in the paper making process.

Pitch containing pulp which can be subjected to the process of the present invention particularly comes from wood pulp, which is the most common material used to make paper. Wood pulp generally comes from softwood trees such as spruce, pine, fir, larch and hemlock, but also some hardwoods such as eucalyptus and birch.

The pitch, which can be controlled according to the present invention may comprise such species as fats and fatty acids, steryl esters and sterols, terpenoids, and waxes. The chemical composition depends on the fibre source, such as variety of tree, and on the seasonal growth from which the sample is produced.

Optionally, additives can be added to the water sample to be treated. These might include agents for pH adjustment, etc.

After the adsorption is completed, the composites formed of surface-treated calcium carbonate, organic material and optional further materials can be separated from the aqueous medium by conventional separation means known to the skilled person such as sedimentation, centrifugation and filtration.

The composite material formed on contacting said surface-treated calcium carbonate with said organic material in an aqueous medium is also an object of the present invention.

Such a composite material finds uses including the use as a filler in paper.

In the case where the composite material is formed following the contact of said surface-treated calcium carbonate with sulphur-comprising petroleum or sulphur-comprising petroleum derivatives, this composite material presents the distinct advantage that when burned, this sulphur is reduced.

The following examples will illustrate the present invention, but are not intended to limit the invention in any way.

EXAMPLES

Measurement Methods

BET Specific Surface Area of a Material (m$^2$/g)

BET specific surface area values were determined using nitrogen and the BET method according to ISO 9277.

Particle Size Distribution (Mass % Particles with a Diameter<X) and Weight Median Grain Diameter ($d_{50}$) of Particulate Material Weight median grain diameter and grain diameter mass distribution of a particulate material were determined via the sedimentation method, i.e. an analysis of sedimentation behaviour in a gravimetric field. The measurement was made with a Sedigraph™ 5100.

The method and the instrument are known to the skilled person and are commonly used to determine grain size of fillers and pigments. The measurement is carried out in an aqueous solution of 0.1% by weight of $Na_4P_2O_7$. The samples were dispersed using a high speed stirrer and ultrasonic.

Suspension pH Measurement

The pH of a suspension was measured at 23° C. using a Mettler Toledo™ Seven Easy pH meter equipped with the corresponding Mettler Toledo™ pH expansion unit and a Mettler Toledo InLab® 730 Expert Pro pH electrode.

A three point calibration (according to the segment method) of the instrument is first made using commercially available buffer solutions having pH values of 4, 7 and 10 at 20° C. (from Aldrich™).

The reported pH values are the endpoint values detected by the instrument (the endpoint is when the measured signal differs by less than 0.1 mV from the average over the last 6 seconds).

Weight Solids (% by Weight) of a Material in Suspension

The weight of solids is determined by dividing the weight of the solid material by the total weight of the aqueous suspension.

The weight of the solid material is determined by weighing the solid material obtained by evaporating the aqueous phase of suspension and drying the obtained material to a constant weight.

Gravimetric Analysis of a Suspension (mg/dm$^3$)

For a gravimetric analysis, a 100 cm$^3$ sample of aqueous phase was placed into a pre-weighed aluminium beaker and dried in an oven (90° C., 24 h) to get a total amount of non-volatile residue in the aqueous phase, i.e. any organic and inorganic material which was not adsorbed on the mineral surface.

Suspension Turbidity Analysis (NTU)

45 cm$^3$ samples were used to analyse turbidity caused by colloidal pitch particles by means of a NOVASINA 155 Model NTM-S (152). This instrument transmits light in the near infrared spectrum through an optical fibre probe where the emerging beam is scattered by small particles in suspension. Light scattered back at 180° is collected by parallel optical fibres in the probe and focused onto a photo-diode. The resulting signal is amplified and displayed directly in Nephelometric Turbidity Units (NTU), defined as the intensity of light at a specified wavelength scattered, attenuated or absorbed by suspended particles, at a method-specified angle from the path of the incident light, compared to a synthetic chemically prepared standard. Interference from ambient light is eliminated by the adoption of a modulated transmission signal, removing the need for light-tight sample handling systems.

Chemical Oxygen Demand (COD, mg $O_2$/dm$^3$)

2 cm$^3$ samples were used to make chemical oxygen demand (COD) analyses, which give a value for the total organic content, i.e. the non-adsorbed organic material. The COD analysis expresses the quantity of oxygen necessary for the oxidation of organic materials into $CO_2$ and was measured using a Lange CSB LCK 014, range 1000-10000 mg dm$^{-3}$ with a LASA 1/plus cuvette.

Streaming Current Detector Equivalency (SCD, µEq/g)

SCD titration measures the charge of the colloidal fraction in suspension and was evaluated using Mütek PCD-02 instrumentation.

Polyelectrolyte Titration (PET, µEq/g)

The polyelectrolyte content in the aqueous suspension is determined using a Memotitrator Mettler DL 55 equipped with a Phototrode DP 660 commercialised by Mettler-Toledo, Switzerland. The measurements of the polyelectrolyte content was carried out by weighing a sample of the calcium carbonate suspension into a titration vessel and diluting said sample with deionized water up to a volume of approximately 40 ml. Subsequently, 10 ml of 0.01 M cationic poly(N,N-dimethyl-3,5-dimethylene-piperidinium chloride) (PDDPC; obtained from ACROS Organics, Belgium) are slowly added under stirring into the titration vessel within 5 min. and than the content of the vessel is stirred for another 20 min. Afterwards the suspension is filtered trough a 0.2 µm mix-ester membrane filter (Ø47 mm) and washed with 5 ml of deionized water. The thus obtained filtrate is diluted with 5 ml of phosphate buffer pH 7(Riedel-de Haën, Germany) and than 0.01 M of a potassium polyvinylsulfate (KPVS; obtained from SERVA Feinbiochemica, Heidelberg) solution is added slowly to the filtrate to titrate the excess of cationic reagent. The endpoint of titration is detected by a Phototrode DP660, which is adjusted to 1200 to 1400 mV in deionized water, prior to such measurement. The charge calculation is carried out according to the following evaluation:

$$Q_{atro} = \frac{((V_{PDDPC} * t_{PDA}) - V_{KPVS}) * (-1000)}{E_P * Fk} [\mu Val/g]$$

$$w_{atro} = -\frac{Q_{atro}}{K_{DM} * 100} [\%]$$

Calculation of the optimal sample weight $E_P = \frac{60}{w_{DM} * K_{DM} * Fk}$ Calculation of adapted sample weight for 4 ml consumption $E_{4\ ml} = \frac{E_1 * 6}{(10 - V_{KPVS, 1})}$

ABBREVIATIONS $E_P$=sample weight [g]
$w_{DM}$=Dispersing agent content in [%]
$K_{DM}$=Dispersing agent constant [µVal/0.1 mg dispersing agent]
Fk=Solids content [%]
$V_{PDDPC}$=Volume PDDPC [ml]
$V_{KPVS}$=Volume KPVS [ml]
$t_{PDDPC}$=Titer PDDPC $E_{DM}$=Dispersing agent weight [mg]
Q=Charge [µVal/g]
$w_{atro}$=Dispersing agent content atro [%]
$E_1$=Sample weight of experiment to be optimised [g]
$V_{KPVS,1}$=experimental consumption KPVS [ml] of experiment to be optimised Ions in Solution (ppm)

The ions in an aqueous medium were measured by ion chromatography using a Dionex DX 120 Ion-Chromatograph.

Zeta Potential (mV)

Zeta potential was measured using a Zetasizer Nano ZS at 25° C. Analysis of the resulting data was conducted in accordance with the Smoluchowski coagulation equation according to M. Smoluchowski: "Drei Vorträge über Diffusion, Brownsche Molekularbewegung and Koagulation von Kolloidteilchen", (Phys Z, 17 (1916) 557-571 and 585-599).

Materials

Sample 1

Sample 1 contained the minerals talc, chlorite and magnesite and originated from Finland. The talc purity was of about 97%, which was confirmed by FT-IR [Perkin Elmer Spectrum One Spectrometer] and X-ray fluorescence (XRF) [ARL 9400 Sequential XRF] analyses.

It was ground with a jet-mill resulting in a BET specific surface area of 9 $m^2g^{-1}$ and a $d_{50}$ of 2.2 µm.

Sample 2

284 g of stearic acid, 89.2 g of 2-Amino-2-methyl-1-propanol (AMP) and 100 g of water were mixed together to form a solution of AMP-stearic acid salt (hereafter "FAS1"). 5,600 g in respect to dry mineral matter of a 70 wt. % solids slurry of marble of Norwegian origin, in which 75% by weight of the particles had a particle diameter of less than 1 µm and a specific surface of 9.2 $m^2$/g, was prepared by dispersing an approximately 70 wt. % solids filter cake of low solids ground (at 20 wt. % in absence of dispersant) marble of such finesse using 0.5 wt. % in respect to dry marble of a sodium salt of acrylic acid-maleic acid copolymer (having a Mw=12 000 g/mol), at room temperature. AMP-stearic acid salt "FAS1" was added at a temperature of 60° C. to the slurry, which was also heated to 60° C., to reach a fatty acid salt addition of 1.0 wt. % based on the dry weight of calcium carbonate. The final solids of the suspension was 68 wt. %, the Brookfield viscosity at 100 rpm measured after 1 min was 300 mPa·s and the pH at 23° C. was 8.34. This product represents a product of according to the invention.

Sample 3

10.12 g of octanoic acid, 6.27 g of 1-amino-2-propanol (AMP) and 17 g of water were mixed together to form a solution of AMP-octanoic acid salt (hereafter "FAS2"). The total of FAS2 was then mixed, at room temperature, with 2,000 g in respect to dry mineral matter of a 20 wt. % solids (wet ground at 20 wt % in absence of dispersant) marble of Norwegian origin, in which 75% by weight of the particles had a particle diameter of less than 1 µm, and having a specific surface of 9.2 $m^2$/g. This corresponded to a fatty acid salt addition of 0.82% by dry weight based on the dry weight of calcium carbonate. This product represents a product of according to the invention.

Sample 4

14.1 g of a mixture of coco nut fatty acids (consisting of 5 wt. % caprylic acid, 6 wt. % capric acid, 52 wt. % lauric acid, 20 wt. % myristic acid, 9 wt. % palmitic acid, 2 wt. % stearic acid, 4 wt. % oleic acid and 2 wt. % linoleic acid), 6.6 g of 1-amino-2-propanol (AMP) and 5 g of water were mixed together to form a solution of AMP-coco nut fatty acid salt (hereafter "FAS3"). The total of FAS3 was then mixed, at room temperature, with 2 000 g, in respect to dry weight of mineral matter, of a 20 wt. % solids (wet ground at 20 wt. % in absence of dispersant) suspension of marble of Norwegian origin, in which 75% by weight of the particles had a particle diameter of less than 1 µm, and having a specific surface of 9.2 $m^2$/g. This corresponded to a fatty acid salt addition of 1.03% by dry weight based on the dry weight of calcium carbonate. This product represents a product of according to the invention.

Sample 5

10.12 g of octanoic acid and 0.7 g of tetraethylenetriamine (TETA) were mixed together to form TETA-octanoic acid salt/octanoic acid mixture (hereafter "FAS4"). The total of FAS4 was then mixed, at room temperature, with 2 000 g, in respect to dry weight of mineral matter, of a 35 wt. % solids (wet ground at 35 wt % in absence of dispersant) suspension of marble of Norwegian origin, in which 75% by weight of the particles had a particle diameter of less than 1 µm and a specific surface of 9.2 $m^2$/g, at room temperature. This corresponded to a fatty acid/fatty acid salt addition of 0.54% by dry weight based on the dry weight of calcium carbonate. This product represents a product of according to the invention.

Sample 6

5 g of FAS 1 was used to dry treat 500 g of dry ground Italian marble having a medium diameter of 1.7 µm. The dry treatment was made in a MTI Mixer activated at 3 000 rpm while heating the product to 130° C. This corresponded to a fatty acid salt addition of 1.0% by dry weight based on the dry weight of calcium carbonate. This product represents a product of according to the invention.

Aqueous Medium Comprising Organic Material

Pitch-Comprising Aqueous Medium 6.0 kg of the fresh wet pulp (3.2 w/w % solids content) were taken from the accept of the screen at a temperature of 90° C. before the bleaching step (peroxide bleaching) at an integrated pulp and paper mill in Switzerland in February 2010. The process water at the sampling position was only circulated in the thermo-mechanical pulp (TMP) plant and contained no fillers. The TMP thus obtained and used as a pitch source for the following experiments consisted of 70 wt.-% spruce, the rest being composed of fir and a small part of pine. The pH of the pulp sample was 6.1 at 25° C. The pulp was wet pressed through a filter of 2 µm pore size (filter paper, circular 602 EH). The filtrate, hereafter "TMP Filtrate", was recovered and analysed; the results are reported in Table 1 below.

TABLE 1

| Property | Value |
|---|---|
| Turbidity (NTU) | 406 |
| COD (mg $O_2$/$dm^3$) | 4070 |
| pH | 7.16 |
| Conductivity (mS/cm) | 0.922 |
| Gravimetry (mg/$dm^3$) | 3160 |
| Zeta potential (mV) | −8.3 +/− 5.36 |
| PET (µEq/g) | −1.62 |
| SCD (µEq/g) | −0.75 |
| Ions in solution (ppm) | |
| $Na^+$ | 131 |
| $K^+$ | 41 |
| $Ca^{2+}$ | 43 |
| $Mg^{2+}$ | 5 |
| $Cl^-$ | 12 |
| $SO_4^{2-}$ | 63 |

Tests in Pitch-Comprising Medium 2.0 g of each of the above listed materials were introduced into flasks along with 200 g samples of TMP Filtrate and with 18.0 g of water. The flasks were then sealed and agitated in a rotating mill (rotating at approximately 100 rpm) for a time period of 2 hours at room temperature.

Thereafter, the contents of each of the flasks were introduced into a Rotina 420 centrifuge, rotating with a relative centrifuge force of 2 580 RCF, and centrifuged for a period of 15 minutes.

Each of the recovered supernatants were analysed for turbidity, COD, gravimetry and ion balance.

TABLE 2

| Sample | 1 | 2 | 3 | 4 | 5 |
|---|---|---|---|---|---|
| Comparative (CO)/Invention (IN) | CO Talc | IN | IN | IN | IN |
| Turbidity (normalized) 100% corresponds to 350 NTU ± 10 NTU | 53% ± 2% | 43% ± 2% | 19 ± 1% | 18% ± 4% | 15% ± 1% |
| COD 100% corresponds to 3644 mg O$_2$/dm$^3$ ± 90 mg O$_2$/dm$^3$ | 90% ± 1% | 92% ± 2% | 87% ± 4% | 86% ± 2% | 88% ± 3% |

The above results show that the surface-treated calcium carbonate of the present invention performs as well or better than talc in order to control wood pitch.

Tests in Oil-Comprising Medium

Prior Art:

600 g of demineralised water was introduced into a glass beaker; then, 20 g of high pressure ASE 55 327/ASE transmission oil (from OL, Bern, Switzerland) was added to form a layer on the top surface of the water. Thereafter, 20 g of talc (Sample 1) was added on top of the oil. The beaker contents were weakly agitated manually using a glass rod.

The oil was mostly bound by the talc mineral and settled to the bottom of the glass beaker. The water bulk and surface remained visibly cloudy.

Invention:

The same protocol as above was repeated, adding 20 g of Sample 6 in place of talc.

The oil was mostly bound by the surface-treated calcium carbonate mineral and settled to the bottom of the glass beaker. The water bulk became visibly clear and no oil could be observed on the water surface.

The invention claimed is:

1. A surface-treated calcium carbonate material obtained by treating at least one calcium carbonate-containing material with at least one salt of a $C_5$-$C_{28}$ fatty acid(s) selected from the group consisting of (i) a mono-alcohol primary alkanolamine salt of a $C_5$-$C_{28}$ fatty acid(s), (ii) a polyethyleneimine salt of a $C_5$-$C_{28}$ fatty acid(s), and (iii) a mixture thereof, to obtain the surface-treated calcium carbonate material.

2. The surface-treated calcium carbonate material according to claim 1, comprising 97 to 99% by weight of a calcium carbonate material, 0.1 to 3% by weight of monoalcohol primary monoalkanol amine and/or polyethyleneimine salt(s) of $C_5$-$C_{28}$ fatty acid(s) and 0 to 1.5% by weight of calcium and/or magnesium salt(s) of $C_5$-$C_{28}$ fatty acid(s).

3. The surface-treated calcium carbonate material according to claim 1, wherein the calcium-carbonate containing material comprises ground natural calcium carbonate, dolomite, precipitated calcium carbonate or any mixture thereof.

4. The surface-treated calcium carbonate material according to claim 1, wherein the calcium-carbonate containing material contains at least 50% by weight of calcium carbonate relative to the total weight of the calcium-carbonate containing material.

5. The surface-treated calcium carbonate material according to claim 1, wherein the calcium-carbonate containing material contains at least 90% by weight of calcium carbonate relative to the total weight of the calcium-carbonate containing material.

6. The surface-treated calcium carbonate material according to claim 1, wherein 30 to 85% by weight of the calcium carbonate material has a particle diameter of less than 1 μm.

7. The surface-treated calcium carbonate material according to claim 1, wherein 60 to 80% by weight of the calcium carbonate material has a particle diameter of less than 1 μm.

8. The surface-treated calcium carbonate material according to claim 1, wherein the calcium carbonate material has a $d_{50}$ value of from 0.4 to 5 μm.

9. The surface-treated calcium carbonate material according to claim 1, wherein the calcium carbonate material has a $d_{50}$ value of from 0.5 to 1 μm.

10. The surface-treated calcium carbonate material according to claim 1, wherein the calcium carbonate material has a BET specific surface area of 1 to 200 m$^2$/g.

11. The surface-treated calcium carbonate material according to claim 1, wherein the calcium carbonate material has a BET specific surface area of 7 to 15 m$^2$/g.

12. The surface-treated calcium carbonate material according to claim 1, wherein the calcium carbonate material is provided in the form of an aqueous suspension.

13. The surface-treated calcium carbonate material according to claim 1, wherein the calcium carbonate material comprises 0.05 to 1 mg dispersant or grinding aid per m$^2$ of calcium-carbonate containing material.

14. The surface-treated calcium carbonate material according to claim 1, wherein the salt of a $C_5$-$C_{28}$ fatty acid(s) is a salt of a $C_6$-$C_{24}$ fatty acid.

15. The surface-treated calcium carbonate material according to claim 1, wherein the salt of a $C_5$-$C_{28}$ fatty acid(s) is a salt of a $C_8$-$C_{18}$ fatty acid.

16. The surface-treated calcium carbonate material according to claim 1, wherein the salt of a $C_5$-$C_{28}$ fatty acid(s) has an iodine number of less than 5 g I$_2$/100 g of fatty acid salt.

17. The surface-treated calcium carbonate material according to claim 1, wherein the salt of a $C_5$-$C_{28}$ fatty acid(s) is a salt of a linear fatty acid if the fatty acid is a $C_6$-$C_9$ fatty acid.

18. The surface-treated calcium carbonate material according to claim 1, wherein the salt of a $C_5$-$C_{28}$ fatty acid(s) is a blend of palmitic acid salt(s) and stearic acid salt(s).

19. The surface-treated calcium carbonate material according to claim 1, wherein the salt of a $C_5$-$C_{28}$ fatty acid(s) is a blend of palmitic acid salt(s) and stearic acid salt(s) in a weight ratio of palmitic acid:stearic acid of 2:1 to 1:2.

20. The surface-treated calcium carbonate material according to claim 1, wherein the salt of a $C_5$-$C_{28}$ fatty acid(s) is a $C_5$-$C_{28}$ fatty acid 30 to 110 mole % neutralized with a monoalcohol primary alkanolamine and/or a polyethyleneimine.

21. The surface-treated calcium carbonate material according to claim 1, wherein the salt of a $C_5$-$C_{28}$ fatty acid(s) is a $C_5$-$C_{28}$ fatty acid 35 to 45 mole % neutralized with polyethyleneimine.

22. The surface-treated calcium carbonate material according to claim 1, wherein the salt of a $C_5$-$C_{28}$ fatty acid(s) is a $C_5$-$C_{28}$ fatty acid 90 to 100 mole % neutralized with a monoalcohol primary alkanolamine.

23. The surface-treated calcium carbonate material according to claim 1, wherein the salt of a $C_5$-$C_{28}$ fatty acid(s) is a polyethyleneimine salt of a $C_5$-$C_{28}$ fatty acid(s), wherein the polyethyleneimine is a linear polyethyleneimine having a molecular weight of from 140 to 700 g/mol.

24. The surface-treated calcium carbonate material according to claim 1, wherein the salt of a $C_5$-$C_{28}$ fatty acid(s) is a polyethyleneimine salt of a $C_5$-$C_{28}$ fatty acid(s), wherein the polyethyleneimine is a linear polyethyleneimine having a molecular weight of from 146 to 232 g/mol.

25. The surface-treated calcium carbonate material according to claim 1, wherein the salt of a $C_5$-$C_{28}$ fatty acid(s) is a monoalcohol primary alkanolamine salt of a $C_5$-$C_{28}$ fatty acid(s).

26. The surface-treated calcium carbonate material according to claim 1, wherein the monoalcohol primary alkanolamine is ethanolamine, propanolamine, butanolamine, pentanolamine or any mixture thereof.

27. The surface-treated calcium carbonate material according to claim 1, wherein the salt of a $C_5$-$C_{28}$ fatty acid(s) is a 1-amino-2-propanol salt of a $C_5$-$C_{28}$ fatty acid.

28. The surface-treated calcium carbonate material according to claim 1, wherein the calcium carbonate material is treated with a total of 0.1 to 3 wt. % of the salt(s) of the $C_5$-$C_{28}$ fatty acid(s), based on the dry weight of the calcium carbonate-containing material.

29. The surface-treated calcium carbonate material according to claim 1, wherein the calcium carbonate material is treated with a total of 0.5 to 2 wt. % of the salt(s) of the $C_5$-$C_{28}$ fatty acid(s), based on the dry weight of the calcium carbonate-containing material.

30. An aqueous medium comprising the surface-treated calcium carbonate material according to claim 1 for the control of organic material in the aqueous medium.

31. Paper comprising the surface-treated calcium carbonate material according to claim 1.

* * * * *